United States Patent [19]

Berg

[11] Patent Number: 5,840,160
[45] Date of Patent: *Nov. 24, 1998

[54] SEPARATION OF 3-CARENE FROM LIMONENE BY EXTRACTIVE DISTILLATION

[76] Inventor: Lloyd Berg, 1314 South Third Ave., Bozeman, Mont. 59715

[*] Notice: The term of this patent shall not extend beyond the expiration date of Pat. No. 5,597,455.

[21] Appl. No.: 761,291

[22] Filed: Dec. 6, 1996

[51] Int. Cl.⁶ .................................. B01D 3/40; C07C 7/08
[52] U.S. Cl. .................................. 203/57; 203/59; 203/60; 203/62; 203/63; 203/64; 203/65; 203/67; 203/68; 203/69; 585/860; 585/864; 585/866; 585/867
[58] Field of Search ..................... 203/57, 65, 68, 203/60, 63, 64, 62, 69, 67, 59; 585/350, 860, 864, 867, 866

[56] References Cited

U.S. PATENT DOCUMENTS

| | | | |
|---|---|---|---|
| 4,245,075 | 1/1981 | Lepert | 526/280 |
| 5,084,142 | 1/1992 | Berg et al. | 203/57 |
| 5,085,739 | 2/1992 | Berg et al. | 203/60 |
| 5,380,405 | 1/1995 | Berg | 203/62 |
| 5,582,693 | 12/1996 | Berg | 203/63 |
| 5,597,455 | 1/1997 | Berg | 585/350 |

*Primary Examiner*—Virginia Manoharan

[57] ABSTRACT

3-Carene is difficult to separate from limonene by conventional distillation or rectification because of the proximity of their boiling points. 3-Carene can be readily separated from limonene by extractive distillation. Effective agents are o-cresol, 2,6-dimethyl-4-heptanone and triethylene glycol.

1 Claim, No Drawings

SEPARATION OF 3-CARENE FROM LIMONENE BY EXTRACTIVE DISTILLATION

FIELD OF THE INVENTION

This invention relates to a method for separating 3-carene from limonene using certain organic compounds as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the highest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The usual method of evaluating the effectiveness of extractive distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, Both Products (Mole Fraction) | Relative Volatility Theoretical Stages at Total Reflux | | | | | | | |
|---|---|---|---|---|---|---|---|---|
| | 1.02 | 1.1 | 1.2 | 1.3 | 1.4 | 1.5 | 2.0 | 3.0 |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 20 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

3-Carene and limonene boil only six degrees apart and are difficult to separate by conventional distillation or rectification. Table 2 shows that with an agent giving a relative volatility of 1.5, only 30 actual plates are required.

TABLE 2

Theoretical And Actual Plates Required vs. Relative Volatility For 3-Carene - Limonene Separation

| Relative Volatility | Theoretical Plates Required At Total Reflux, 99% Purity | Actual Plates Required, 75% Eff. |
|---|---|---|
| 1.2 | 49 | 66 |
| 1.35 | 31 | 42 |
| 1.5 | 22 | 30 |

OBJECTIVE OF THE INVENTION

The object of this invention is to provide a process or method of extractive distillation that will enhance the relative volatility of 3-carene from limonene in their separation in a rectification column. It is a further object of this invention to identify effective extractive distillation agents that are stable and can be recycled.

SUMMARY OF THE INVENTION

The objects of this invention are provided by a process for the separation of 3-carene from limonene which entails the use of certain organic compounds when employed as the agent in extractive distillation.

DETAILED DESCRIPTION OF THE INVENTION

I have discovered that certain organic compounds will effectively increase the relative volatility between 3-carene and limonene during rectification when employed as the agent in extractive distillation. Table 3 summarizes the data obtained with these agents. The agents which are effective are phenol, m-cresol, p-cresol, 3-ethyl phenol, o-cresol, 2,6-dimethyl phenol, tetra ethyl ortho silicate, 1-octanol, sec. phenyl alcohol, acetophenone, 2,6-dimethyl-4-heptanone, propiophenone, diethylene glycol methyl ether, diethylene glycol butyl ether, triethylene glycol, polyethylene glycol 300, polyethylene glycol 400, tripropylene glycol methyl ether, benzyl ether, 1,2-diaminocyclohexane, 1,2-methylene dioxybenzene, phenyl ether, methyl n-amyl ketoxime, adiponitrile, 1,1,3,3-tetramethyl urea, nitrobenzene, 2-nitrotoluene, 3-nitrotoluene and triacetin.

TABLE 3

Effective Extractive Distillation Agents 3-Carene - Limonene

| Compounds | Relative Volatility |
|---|---|
| None | 1.25 |
| Phenol | 1.6 |
| o-Cresol | 1.55 |
| m-Cresol | 1.45 |
| p-Cresol | 1.45 |
| 3-Ethyl phenol | 1.35 |
| 2,6-Dimethyl phenol | 1.4 |
| Tetra ethyl ortho silicate | 1.35 |
| 1-Octanol | 1.35 |
| sec. Phenyl alcohol | 1.35 |
| Acetophenone | 1.35 |
| 2,6-Dimethyl-4-heptanone | 1.6 |
| Propiophenone | 1.45 |
| Diethylene glycol methyl ether | 1.6 |
| Diethylene glycol butyl ether | 1.35 |
| Triethylene glycol | 1.5 |

TABLE 3-continued

Effective Extractive Distillation Agents
3-Carene - Limonene

| Compounds | Relative Volatility |
| --- | --- |
| Polyethylene glycol 300 | 1.5 |
| Polyethylene glycol 400 | 1.4 |
| Benzyl ether | 1.45 |
| 1,2-Methylene dioxybenzene | 1.35 |
| Phenyl ether | 1.4 |
| 1,2-Diamino cyclohexane | 1.45 |
| Methyl n-Amyl ketoxime | 1.4 |
| Adiponitrile | 1.35 |
| 1,1,3,3-Tetramethyl urea | 1.35 |
| Nitrobenzene | 1.35 |
| 2-Nitrotoluene | 1.35 |
| 3-Nitrotoluene | 1.45 |
| Triacetin | 1.4 |

THE USEFULNESS OF THE INVENTION

The usefulness or utility of this invention can be demonstrated by referring to the data presented in Tables 1,2 and 3. All of the successful agents show that 3-carene can be separated from limonene by means of extractive distillation and that the ease of separation is considerable.

WORKING EXAMPLE

Example 1

Fifty grams of a 3-carene-limonene mixture and fifty grams of o-cresol as the extractive distillation agent were charged to a vapor-liquid equilibrium still and refluxed for three hours. The vapor composition was 39.5% carene and 60.5% limonene; the liquid composition was 29.2% 3-carene and 70.8% limonene. This is a relative volatility of 1.55.

I claim:

1. A method for recovering 3-carene from a mixture of 3-carene and limonene which consists essentially of distilling a mixture of 3-carene and limonene in the presence of an extractive distillation agent, recovering the 3-carene as overhead product and obtaining the limonene and the extractive distillation agent as bottoms product, wherein said extractive distillation agent consists of one material selected from the group consisting of phenol, o-cresol, m-cresol, p-cresol, 3-ethyl phenol, 2,6-dimethyl phenol, tetra ethyl ortho silicate, 1-octanol, sec. phenyl alcohol, acetophenone, 2,6-dimethyl-4-heptanone, propiophenone, diethylene glycol methyl ether, diethylene glycol butyl ether, triethylene glycol, polyethylene glycol 300, polyethylene glycol 400, benzyl ether, 1,2-Methylene dioxybenzene, phenyl ether, 1,2-diamino cyclohexane, methyl n-amyl ketoxime, adiponitrile, 1,1,3,3-tetramethyl urea, nitrobenzene, 2-nitrotoluene, 3-nitrotoluene and triacetin.

* * * * *